US005833983A

United States Patent [19]
Waldmann et al.

[11] Patent Number: 5,833,983
[45] Date of Patent: Nov. 10, 1998

[54] INTERLEUKIN 2 RECEPTOR AND APPLICATIONS THEREOF

[75] Inventors: Thomas A. Waldmann, Silver Spring; Warren J. Leonard, Bethesda, both of Md.

[73] Assignee: The United States of America as represented by the Secretary of Dept. of Health and Human Services, Washington, D.C.

[21] Appl. No.: 463,491

[22] Filed: Jun. 5, 1995

Related U.S. Application Data

[62] Division of Ser. No. 653,477, Feb. 11, 1991, abandoned, which is a division of Ser. No. 588,498, Sep. 27, 1990, which is a division of Ser. No. 165,302, Mar. 8, 1988, abandoned, which is a continuation of Ser. No. 66,989, Jun. 29, 1987, abandoned.

[51] Int. Cl.$^6$ .......................... C07K 16/28; C07K 16/46; A61K 39/395

[52] U.S. Cl. ...................... 424/130.1; 424/138.1; 424/143.1; 424/154.1; 424/156.1; 424/178.1; 424/181.1; 424/183.1; 530/387.7; 530/387.1; 530/388.22; 530/388.75; 530/388.8; 530/388.85; 530/389.6; 530/389.7

[58] Field of Search ............................ 424/134.1, 130.1, 424/138.1, 143.1, 154.1, 156.1, 178.1, 181.1, 183.1; 530/391.3, 391.7, 387.7, 387.1, 388.22, 388.8, 388.85, 389.6, 389.7

[56] References Cited

U.S. PATENT DOCUMENTS 5,352,772  10/1994  Smith ........................................ 530/350

OTHER PUBLICATIONS

Tsudo et al., Proc. Natl. Acad. Sci. USA 83:9694–9698, 1986.
Waldmann, Science 232:727–732, 1986.
Waldmann, Cellular Immunology 99:53–60, 1986.
Greene et al. Annals of Internal Medicine 105:560–572, 1986.
Waldmann, et al. Haematology and Blood Transfusion 31:110–115, 1987.
Siegel, et al. Science 238:75–78, 1987.
Waldmann, Environmental Health Perspectives 75:11–15, 1987.
Tsudo, et al. Proc. Natl. Acad. Sci USA 84:5394–5398, 1987.
Tsudo et al., Proc. Natl. Acad. Sci. USQ 84:4215–4218, 1987.
Robb et al. Journal of Experimental Medicine 165:1201–1206, 1987.
Robb et al. Proc. Natl. Acad. Sci. USA 84:2002–2006, 1987.
Teshigaware et al. J. Exp. Med. 165:223–238, 1987.
Wornmann, Bernhard et al. "Structure/Function Analyses of IL–2 Binding proteins on Human B Cell Percursor Acute Lymphoblastics Leukemias", Chemical Abstracts, vol. 108, 1988, p. 456.
Kozak et l. Proc. Natl. Acad. Sci. USA 83:474,478, 1986.
Kronke et al. Cancer Research 46:3295–3298, 1986.
Sugie et al. "The Signal Transduction at Interleukin–2(IL–2) Receptor: On the Roles of Two Types of IL–2 Receptors", Sch. Med., 1987: CA107(25):23458m.
Sharon et al. "Novel Interleukin–2 Receptor Subunit Detected by Cross–Linking Under High–Affinity Conditions", Reports, Nov. 14, 1986, pp. 859–863.
Herrmann et al. "The Mouse High Affinity IL 2 Receptor Complex", Immunobiology, 175(3), 1987, 145–58.
Osawa et al. "Partial Characterization of the Putative Rat Interleukin 2 Receptor", Eur. J. Immunol. 1984, 14:374:376.
Dukovich et al. "A Second Human Interleukin–2 Binding Protein That May be a Component of High–Affinity Interleukin–2 Receptors", Nature, Vol. 327, 11 Jun. 1987, pp. 518–522.
Robb et al. "Internalization of Interleukin 2 is Mediated by the B Chain of the High–Affinity Interleukin 2 Receptor", J. Exp. Med., 1987, 165:1201–1206.
Tsudo et al. "Demonstration of a Non–Tac Peptidinding Protein That May be a Component of High–Affinity Interleukin–2 Receptors", Nature, vol. 327, 11 Jun. 1987, pp. 518–522.
Kozak, R.W. et al. 1986. PNAS USA 83:474–478.
Kronke, M. et al. 1986. Cancer Res. 46:3295–3298.

*Primary Examiner*—Toni R. Scheiner
*Assistant Examiner*—Nancy A. Johnson
*Attorney, Agent, or Firm*—Morgan & Finnegan, LLP

[57] ABSTRACT

The present invention is related to the field of receptor molecules and complexes. More particularly, the present invention is related to a new polypeptide receptor for interleukin-2 having a molecular weight of about 70–75,000, which is a component of the high affinity IL-2 receptor, antibodies against this new polypeptide, and recombinant interleukins capable of binding to the new receptor. Various applications of the p70-75 receptor, the anti-p70-75 antibodies and IL-2W$_1$ and IL2W$_2$ have also been described.

2 Claims, 1 Drawing Sheet

INTERLEUKIN 2 RECEPTOR AND APPLICATIONS THEREOF

This is a divisional of U.S. Ser. No. 07/653,477 filed Feb. 11, 1991 (abandoned) which is a divisional application of U.S. Ser. No. 07/588,498 filed Sep. 27, 1990 which is a divisional application of U.S. Ser. No. 07/165,302 filed Mar. 8, 1988 (abandoned) which is a continuation of U.S. Ser. No. 07/066,989 filed Jun. 29, 1987 (abandoned).

BACKGROUND OF THE INVENTION

1. Technical Field

The present invention is related to the field of receptor molecules and complexes. More particularly, the present invention is related to a new polypeptide receptor for interleukin-2 (IL-2) having a molecular weight of about 70–75,000, which is also a component of the high affinity IL-2 receptor. The invention further relates to antibodies against this new polypeptide and recombinant interleukins which have binding affinity for the new receptor.

2. State of the Art

There are at least two categories of cells which respond to interleukin-2 (IL-2). The first category includes those types of cells which must express high affinity IL-2 receptors and express the Tac antigen (defined by anti-Tac monoclonal antibody, denoted herein as p55) for interaction with IL-2 and are designated herein as "Tac-positive" cells. An example of a Tac-positive cell is the activated T cell.

The second category includes those types of cells which do not express high affinity IL-2 receptors or p55, but interact with IL-2 by expressing a novel glycoprotein, designated herein as "p70-75", which is distinct and different from p55. Examples of p55 negative p70-75 expressing cells are resting large granular lymphocytes (LGL), natural killer (NK) and precursors of lymphokine-activated-killer (LAK) cells.

A review of the structure, function and role of IL-2 receptors can be found in Waldmann (Science, 232:727–732, 1986; Cell mmunol. 99:53–60, 1986) and Greene and Leonard (Ann Rev Immunol 4:69–95, 1986).

The discovery of p70-75 and elucidation of its nature, function and use in biological systems is the subject matter of the present invention.

SUMMARY OF THE INVENTION

It is, therefore, an object of the present invention to provide a new p70-75 peptide having binding affinity for IL-2 at an epitopic site different from that of the p55.

It is a further object of the present invention to provide antibodies having specific binding affinity for p70-75.

It is another object of the present invention to provide an altered IL-2 molecule, designated "IL-2W$_1$", having epitopes required for binding with the p70-75 but devoid of epitopes required for binding with the p55.

It is a still further object of the present invention to provide altered IL-2 molecule, designated "IL-2W$_2$", having epitopes required for binding with the p55 peptide but devoid of epitopes required for binding with the p70-75 peptide.

It is an additional object of the present invention to provide a method of producing LAK cells by reacting LGL cells with IL-2W$_1$.

It is yet another object of the present invention to provide a method of destroying LAK-susceptible cells by contacting said LAK-susceptible cells with LAK cells produced by reacting LGL cells with IL2-W$_1$.

A still further object of the present invention is to provide a pharmaceutical composition comprising an effective amount of LAK cells, produced by reacting LGL cells with IL2-W$_1$, to destroy LAK-susceptible cells; and a pharmaceutically acceptable carrier. This combination may optionally further contain IL2-W$_1$ in an amount sufficient to maintain sustained killer activity of LAK cells.

Various other objects and advantages of the present invention will become apparent from the Detailed Description of the Invention.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
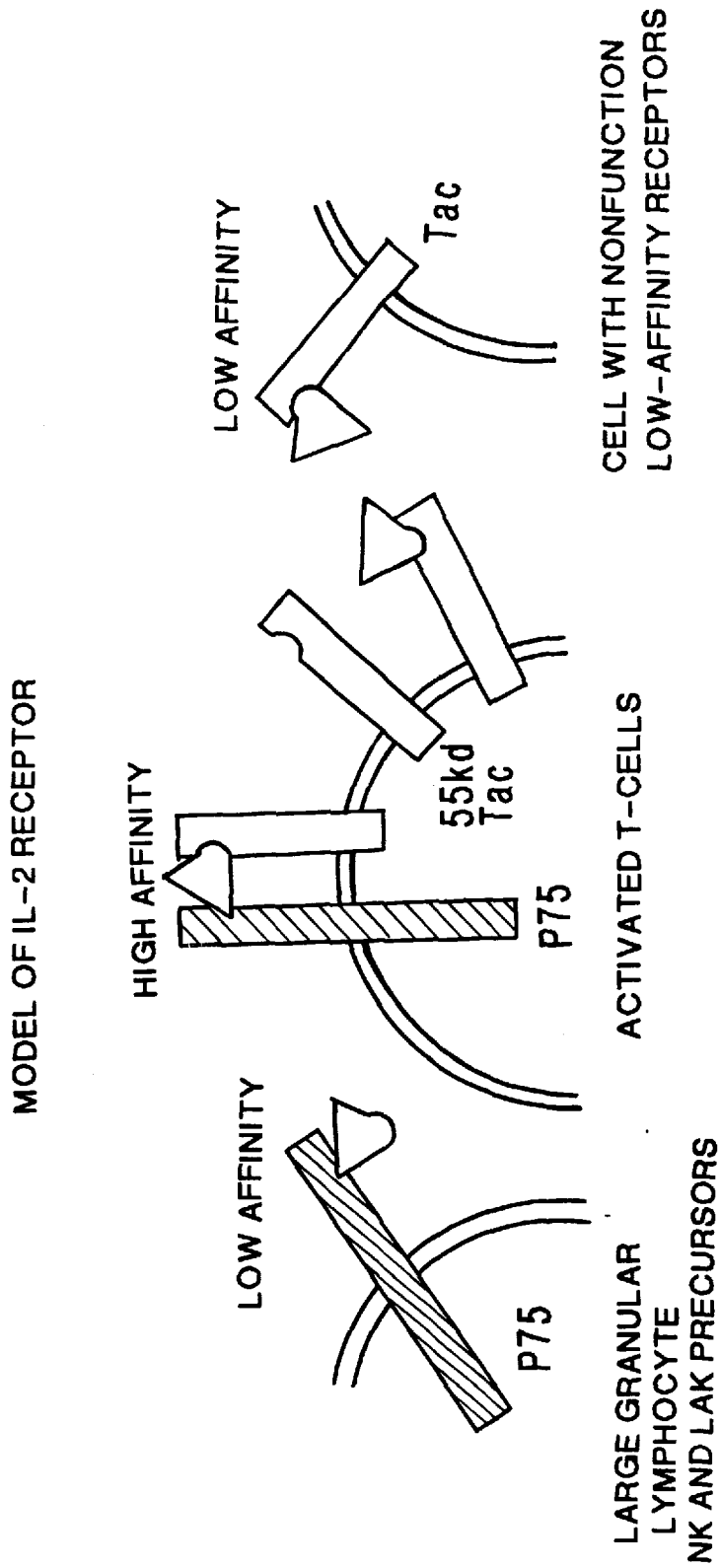
FIG. 1 is a schematic representation of a multichain model of IL-2 receptor in which an independently existing p55 or p70-75 represent low and intermediate affinity receptors, respectively, whereas high affinity receptors are present when both p55 and p70-75 are associated in a receptor complex. Cell lines, as shown on the right that express only the p55 and low affinity receptors, do not respond to the IL-2. Activated T cells as shown in the center express both p55 and p70-75 and manifest high affinity receptors. Such high affinity receptors are required for certain T cell functions. Certain cells such as lymphokine activated killer precursor cells and natural killer cells express only the p70-75 peptide as shown on the left and manifest intermediate affinity receptors. Such cell types can respond to IL-2 utilizing the p70-75 IL-2 binding peptide alone.

The above and various other objects and advantages of the present invention are achieved by a polypeptide characterized by a molecular weight of about 70–75,000 and which binds specifically to an epitope contributed to by amino acids 1–25 of interleukin 2.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

Of course, apart from being distinct from the p55, the p70-75 of the present invention has the following additional properties.

(a) A mouse monoclonal antibody L34 that is directed toward the region of amino acids 1 to 25 of IL-2 precipitated unbound IL-2 and IL-2 bound to p55, but did not precipitate IL-2 bound to p70-75 suggesting that amino acids 1–25 are the part of IL-2 bound by p70-75. In a parallel study, a polyclonal rabbit antiserum directed toward amino acids 30–55 of IL-2 precipitated IL-2 and IL-2 bound to p70-75 but did not precipitate IL-2 bound to Tac peptide.

These results suggest that amino acids 1–25 of IL-2 are involved in the binding to p70-75.

(b) LGL cells obtained from normal human peripheral blood express the p70-75 peptide alone, that is this cell population expresses an IL-2 receptor (P70-75), which is not recognized by anti-Tac monoclonal antibody.

(c) LGL leukemic cells manifest only p70-75 and not p55.

(d) Even in Tac-negative but IL-2 dependent cell line (such as LGL leukemia cells), it was discovered that IL-2 can provide Tac-inducing signal through the p70-75 peptide by upregulation so that transduction, both at the mRNA and protein level, occurs resulting in newly expressed p55 in the initially Tac-negative cells. Without being bound to any theory, such results from Tac-negative cells lead to the postulation that once the p55 is produced, p55 then associates with the P70-75 peptide, the resulting combination of p70-75 plus p55 forming the high-affinity IL-2 receptor which in turn is then readily inhibited by anti-Tac antibody.

Preferred materials and methods and various experiments which support some of the findings noted above are described in Sharon et al (Science, 234:859–863, 1986) and Tsudo et al (Proc. Natl. Acad. Sci. USA, 83:9694–9698, 1986) and the same is incorporated herein by reference.

Preparation of monoclonal antibodies against the p75 peptide.

Two approaches are used to prepare monoclonal antibodies against the p70-75 peptide. (a) Cell lines MLA 144 or HUT 78 that express the p70-75 peptide are injected into 8 week old female Balb/c mouse on two occasions with a three week interval. $1 \times 10^6$ viable cells in 0.2 ml of RPMI 1640 culture media are injected. Cell fusion is performed at three days after the second injection. Spleen cell suspension are obtained by teasing of the spleen and lysis of red blood cells with standard ACK lysing buffer (155 mM $NH_4Cl$, 10 mM $KHCO_3$, 0.1 mM $Na_2$-EDTA and distilled water). Cell fusions are carried out according to the standard procedure of Kohler and Milstein (*Nature* 256:495, 1975). 150 million spleen cells are fused with $3 \times 10^7$ NS1 mouse myeloma cells using 30% polyethylene glycol (MW 1,000, Backers, Philipsburg, N.J.) dissolved in Delbecco's Modified Eagle's Media. Cells are resuspended in medium and are distributed into flat bottom microtiter plates where they are selected by feeding with HAT media containing 0.1 mM hypoxanthine, 0.4 uM aminopterin, 16 mM thymidine. Fifteen days after cell fusion the culture supernatants from the wells are tested for antibody activity by an ELISA technique to determine reactivity aginst cell lines (e.g. MLA 144 and HUT 78) that express the p70-75 and non-reactivity against cell lines (e.g. MT-1) that do not express p55. After screening, hybridoma cultures that showed an appropriate pattern of reactivity, are expanded and cloned by a limiting dilution method. Fourteen days later when hybridoma clones are expanded, the supernantants are tested again for their reactivity against the same target cells. Two specific systems are used to define blocking and non-blocking antibodies to p70-75. Blocking antibodies are defined by their ability to inhibit the binding of radioactive IL-2 to cell lines such as MLA 144 that express p70-75 but not p55. Non-blocking antibodies are defined by their ability to precipitate radiolabelled IL-2 crosslinked to p70-75. Of course, radiolabelled IL-2 can be easily prepared by routine standard procedures well known in the art.

(b) In the second procedure anti-idiotype antibodies to antibodies that are directed toward IL-2 are prepared. In such studies, the immunogen is an antibody to the part of the IL-2 molecule that is involved in IL-2 binding to the p70-75. Such anti-IL-2 antibodies are defined by their ability to bind to unbound IL-2 or IL-2 bound to p55 but are unreactive to IL-2 bound by crosslinking to p70-75. Antibodies to the idiotype of such antibodies toward IL-2 also crossreact with the part of the p70-75 IL-2 binding receptor involved in IL-2 binding. For such studies, the procedure for the production of a monoclonal antibody vide supra is utilized with the exception that use is made of the monoclonal antibody directed toward IL-2 as the immunogen in lieu of the cell lines expressing p70-75.

It should be noted that various modifications of the p70-75 antibodies such as conjugating the p70-75 antibodies with cytotoxic agents (for instance with ricin A or salmonella toxin or cytotoxic radionuclides and the like) to impart cytotoxic properties to the antibodies are easily achieved by routine and standard methods well known in the art. Apart form being useful in the purification of p70-75, antibodies of the present invention, including the cytotoxic antibodies, are useful in neutralizing or killing p70-75 expressing cells such as p70-75 expressing leukemias and those conditions (such as autoimmune disease or organ allograft protocols) which arise due to the abnormal interaction or pathophysiology caused by the expression of p70-75.

Isolation and Purification of p70-75

The p70-75 is obtained from any of the Tac-negative, IL-2 responsive cell lines, a few examples of which have been mentioned herein above. Anti-p70-75 and a control monoclonal UPC10 (a monoclonal non-reactive with T cells) are used to generate immunoaffinity columns. Imunoaffinity columns are prepared by coupling purified anti-p70-75 and UPC10 monoclonal antibodies to cyanogen bromide activated sepharose. HUT-78 cells are grown in 10% fetal bovine serum/RPMI media collected by ultrafiltration washed twice in phosphate buffered saline and solubized in an extraction buffer containing 10 mM Tris pH 7.4, 0.15M sodium chloride 100 micrograms $ml^{-1}$ phenylmethyl sulfonylfluoride (PMSF) 1% Triton-X-100. Extracts are centrifuged and the top lipid layer is discarded. The remaining supernatant is passed over a UPC10 column four times and then over an anti-p70-75 column three times. The anti-p70-75 column is washed with extraction buffer, then with 10 mM Tris pH 7.5, 0.5M NaCl, 1% Triton-X-100, then with 10 mM Tris pH 7.5, 0.2% triton-X-100 and then with 10 mM of Tris pH 7.5. The anti-p70-75 column is then eluted with 2.5% (v/v) acetic acid. The eluted protein is lyophilized, resuspended in phosphate buffered saline and an aliquot is analyzed on SDS-polyacrylamide gels under reducing conditions: Gels are silver stained to assess the yield and purity.

Preparation of Altered IL-2

IL-$2W_1$ molecules that bind to p70-75 alone and IL-$2W_2$ molecules that bind to p55 alone are generated by constructing mutants by site directed mutagenesis. For both IL-2 analogs 18 bases long oligonucleotide chains are synthesized using commercially available DNA synthesizers. The oligonucleotides are complementary to the DNA of the IL-2 gene that has been cloned and is available with the exception that they contain 1–2 mismatches. In the presence of the DNA primer and the four nucleotide precursors of the DNA, the slightly mismatched short DNA segments can function as primers for DNA extention when added to the circular single stranded chains of M13 phage. The resulting complete double stranded DNA will be perfectly complementary except for the mismatched bases at the primer site. After entry into *E. coli*, DNA replication generates two types of daughter DNA strands; wild type strands and mutant strands, the latter containing changes imposed by the mismatched primer. The strands can be easily distinguished by the way they bind the corresponding oligonucleotides. Wild type daughter DNAs bind more strongly to wild type oligonucleotide while the short DNA segment that primes the mutant sequences will bind best to the mutated progeny strands that are to be selected. To generate IL-2W$_1$ that binds to p70-75 but not to the p55, mutations are generated in the peptide region involved in binding to p55. In a complementary study, IL-2W$_2$ that binds to p55 but not to the p70-75 peptide is generated using a slightly mismatched oligonucleotide that has a mismatch at the bases encoding the amino acids involved in binding to p70-75 but not at the site involved in binding to p55.

Activation of NK or LAK cells

To activate natural killer (NK) and lymphokine activated killer (LAK) cells without activating T lymphocytes, IL-2W$_1$ is selectively and advantageously employed. At present lymphokine activated killer cells are generated by incubating peripheral blood mononuclear cells with natural IL-2. The activated cells are then readministered to the patient along with daily intravenous doses of IL-2. Certain cancer patients, especially those with renal tumors and melanoma, respond to this therapy; however, there is marked toxicity associated with this approach. A part of this toxicity is considered to be due to the activation of T cells following the interaction of native IL-2, and secretion by these T cells of toxic lymphokines. The present invention for the first time provides means for producing LAK cells without inducing the production of toxic lymphokines. In accordance with the present invention, IL-2W$_1$, which interacts only with the p70-75, is substituted in vitro and/or in vivo for natural IL-2 for the generation and maintenance of LAK cells. IL-2W$_1$ binds to the p70-75 which is the receptor for IL-2 on large granular lymphocytes (the precursors of natural killer and lymphokine activated killer cells) and is sufficient for IL-2 activation of these cells. In contrast, many T cell functions depend on the simultaneous binding of IL-2 to the p55 and p70-75 IL-2 binding peptides of the high affinity receptor complex. Since IL-2W$_1$ does not bind to the Tac peptide, it does not activate T-cells at the concentrations used. Thus, IL-2W$_1$ activates the large granular lymphocytes to become effective natural killer and lymphokine activated killer cells without simultaneously activating T lymphocytes to become activated cells that synthesize toxic lymphokines. Thus, with this recombinant lymphokine IL-2W$_1$ in contrast to natural IL-2, the desired lymphokine activated killer cells to destroy the tumor cell populations are activated without activating T lymphocytes and their toxic lymphokine.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for neutralizing or killing p70-75 expressing cells, comprising reacting p70-75 expressing cells with an effective amount of anti-p70-75 antibody to neutralize or kill p70-75 expressing cells.

2. The method of claim 1 wherein said antibody is conjugated with a cytotoxic ligand.

* * * * *